(12) United States Patent
Takken et al.

(10) Patent No.: US 10,912,623 B2
(45) Date of Patent: *Feb. 9, 2021

(54) STERILIZATION TRAY PROTECTION MECHANISMS

(71) Applicant: O&M Halyard, Inc., Mechanicsville, VA (US)

(72) Inventors: Wendy Takken, Alpharetta, GA (US); Ajay Houde, Johns Creek, GA (US); Audra Wright, Woodstock, GA (US); Khoa Lien, Alpharetta, GA (US); Joe Cesa, Cumming, GA (US); Anthony Stephen Spencer, Woodstock, GA (US); Paige O'Shea, Alpharetta, GA (US)

(73) Assignee: O&M Halyard, Inc., Mechanicsville, VA (US)

( * ) Notice: Subject to any disclaimer, the term of this patent is extended or adjusted under 35 U.S.C. 154(b) by 351 days.

This patent is subject to a terminal disclaimer.

(21) Appl. No.: 15/748,858

(22) PCT Filed: Aug. 13, 2015

(86) PCT No.: PCT/US2015/044957
§ 371 (c)(1),
(2) Date: Jan. 30, 2018

(87) PCT Pub. No.: WO2017/027032
PCT Pub. Date: Feb. 16, 2017

(65) Prior Publication Data
US 2018/0228565 A1    Aug. 16, 2018

(51) Int. Cl.
*A61B 50/33*     (2016.01)
*A61L 2/26*      (2006.01)
(Continued)

(52) U.S. Cl.
CPC .............. *A61B 50/33* (2016.02); *A61B 50/30* (2016.02); *A61L 2/26* (2013.01);
(Continued)

(58) Field of Classification Search
CPC .......... B65D 81/053–056; A61B 50/30; A61B 50/33; A61B 2050/002; A61B 2090/037;
(Continued)

(56) References Cited

U.S. PATENT DOCUMENTS 2,734,543 A    2/1956 Hunter
3,770,119 A    11/1973 Hultberg et al.
(Continued)

FOREIGN PATENT DOCUMENTS

| | | |
|---|---|---|
| AU | 2010100500 | 9/2010 |
| GB | 2 378 129 A | 2/2003 |
| WO | WO 2005/037333 A1 | 4/2005 |

OTHER PUBLICATIONS

International Search Report and Written Opinion for PCT/US2015/044957, dated Apr. 8, 2016, 13 pages.
Co-Pending U.S. Appl. No. 15/748,871, filed Jan. 30, 2018.

*Primary Examiner* — Chun Hoi Cheung
*Assistant Examiner* — Brijesh V. Patel
(74) *Attorney, Agent, or Firm* — Dority & Manning, P.A.

(57) ABSTRACT

A sterilization wrap system with features for protecting a sterilization wrap and/or a sterilization tray of the sterilization wrap system is provided. Such features include strap or belt protectors, edge protectors, corner protectors, and/or expandable protectors, which each may provide protection of one or more areas of the sterilization wrap and/or tray when positioned against an outer surface of the wrap and/or between an inner surface of the wrap and a container for holding implements to be sterilized. A size-selectable protection system also is provided. The size-selectable protec- (Continued)

tion system provides a material having a plurality of perforations such that a length of the material may be selected and detached from the rest of the material. The selected length of material may be used with a sterilization wrap system to protect a sterilization wrap and/or sterilization tray from cuts, tears, or the like.

7 Claims, 8 Drawing Sheets

(51) Int. Cl.
  *A61B 50/30* (2016.01)
  *A61B 90/00* (2016.01)
  *A61B 50/00* (2016.01)

(52) U.S. Cl.
  CPC ... *A61B 2050/002* (2016.02); *A61B 2090/037* (2016.02); *A61B 2090/0807* (2016.02); *A61L 2202/182* (2013.01)

(58) Field of Classification Search
  CPC ............... A61B 2090/0807; A61L 2/26; A61L 2202/181; A61L 2202/182; A61L 2202/24
  USPC ........ 206/363–366, 370, 438, 439, 453, 586
  See application file for complete search history.

(56) References Cited

U.S. PATENT DOCUMENTS

| | | | | |
|---|---|---|---|---|
| 3,991,881 | A | 11/1976 | Augurt | |
| 4,041,203 | A | 8/1977 | Brock et al. | |
| 4,705,171 | A * | 11/1987 | Eldridge | A61F 15/001 |
| | | | | 128/846 |
| 4,706,839 | A * | 11/1987 | Spence | A61L 2/26 |
| | | | | 206/438 |
| 4,876,841 | A * | 10/1989 | Jensen | B65D 71/0096 |
| | | | | 53/399 |
| 5,015,251 | A * | 5/1991 | Cherubini | A44B 18/0003 |
| | | | | 128/DIG. 15 |
| 5,325,987 | A | 7/1994 | Alpern et al. | |
| 5,356,006 | A * | 10/1994 | Alpern | B65D 5/302 |
| | | | | 206/363 |
| 5,435,971 | A | 7/1995 | Dyckman | |
| 5,459,978 | A | 10/1995 | Weiss et al. | |
| 5,635,134 | A | 6/1997 | Bourne et al. | |
| 5,688,476 | A | 11/1997 | Bourne et al. | |
| 6,406,764 | B2 | 6/2002 | Bayer | |
| 6,517,916 | B1 | 2/2003 | Bayer et al. | |
| 7,074,180 | B2 | 7/2006 | Bertolero et al. | |
| 7,780,136 | B2 | 8/2010 | Curnow et al. | |
| 7,798,323 | B1 * | 9/2010 | McCann | A61F 17/00 |
| | | | | 206/370 |
| 9,062,914 | B2 | 6/2015 | Sweeney | |
| 9,119,611 | B2 | 9/2015 | Super et al. | |
| 9,296,535 | B2 * | 3/2016 | Gaynor | A61B 50/00 |
| 9,517,870 | B2 * | 12/2016 | Lien | B65B 11/58 |
| D874,678 | S * | 2/2020 | Haines | D24/231 |
| 2004/0159568 | A1* | 8/2004 | Rutledge | B65D 81/18 |
| | | | | 206/438 |
| 2006/0280891 | A1 | 12/2006 | Swannell | |
| 2007/0003726 | A1 | 1/2007 | Swannell | |
| 2007/0026472 | A1 | 2/2007 | Prokash et al. | |
| 2007/0095699 | A1* | 5/2007 | Frieze | A61B 50/30 |
| | | | | 206/438 |
| 2008/0253947 | A2 | 10/2008 | Davis | |
| 2011/0005647 | A1* | 1/2011 | Campfield | B65D 65/10 |
| | | | | 150/154 |
| 2011/0052863 | A1 | 3/2011 | Sweeney | |
| 2012/0187012 | A1 | 7/2012 | Tevault et al. | |
| 2013/0042576 | A1 | 2/2013 | Sweeney | |
| 2014/0027330 | A1 | 1/2014 | Lavelle | |
| 2015/0021212 | A1 | 1/2015 | Landgrebe et al. | |
| 2015/0021340 | A1 | 1/2015 | Super et al. | |
| 2017/0281815 | A1* | 10/2017 | Hinora | A61L 2/07 |

* cited by examiner

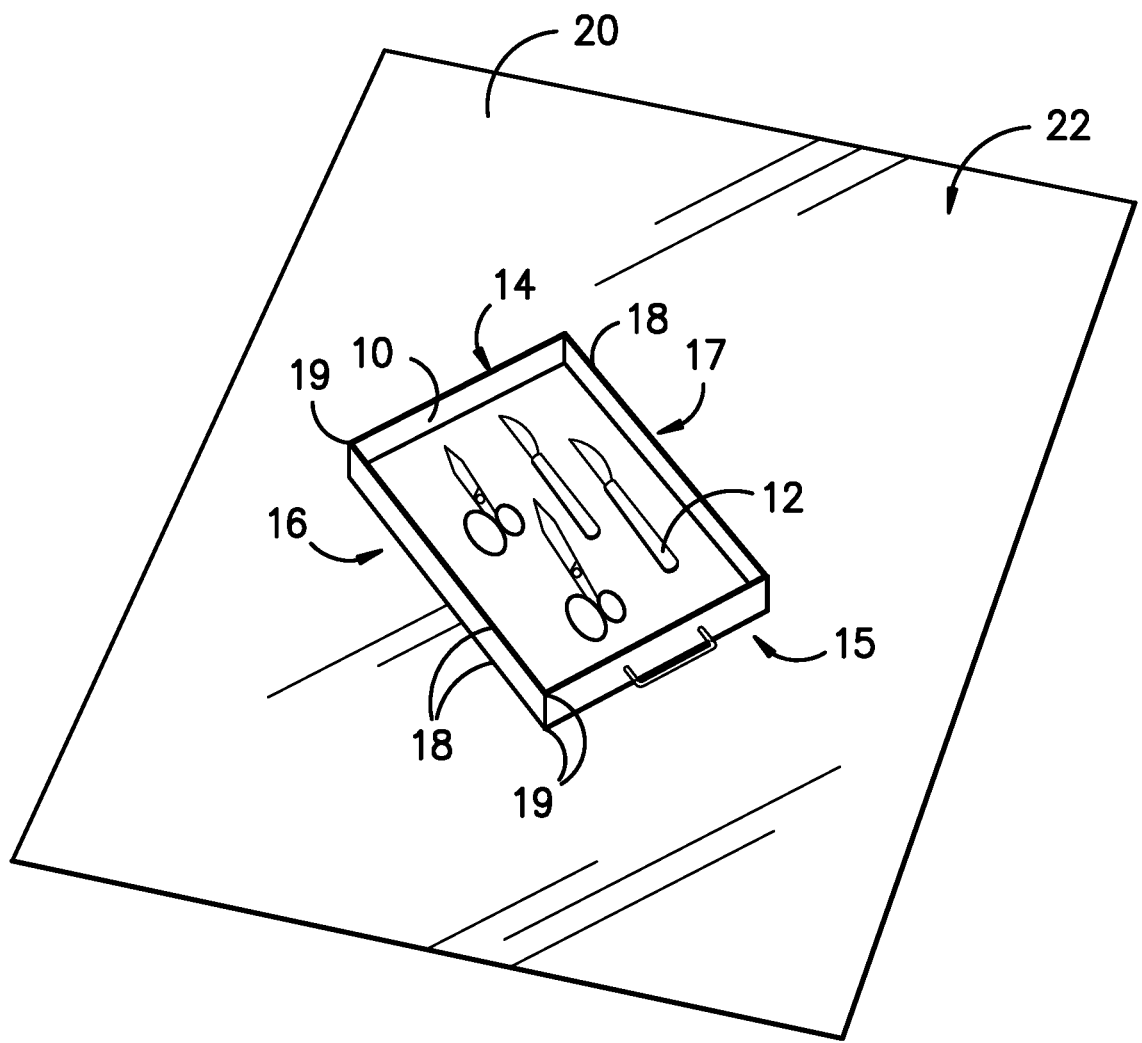
FIG. -1-

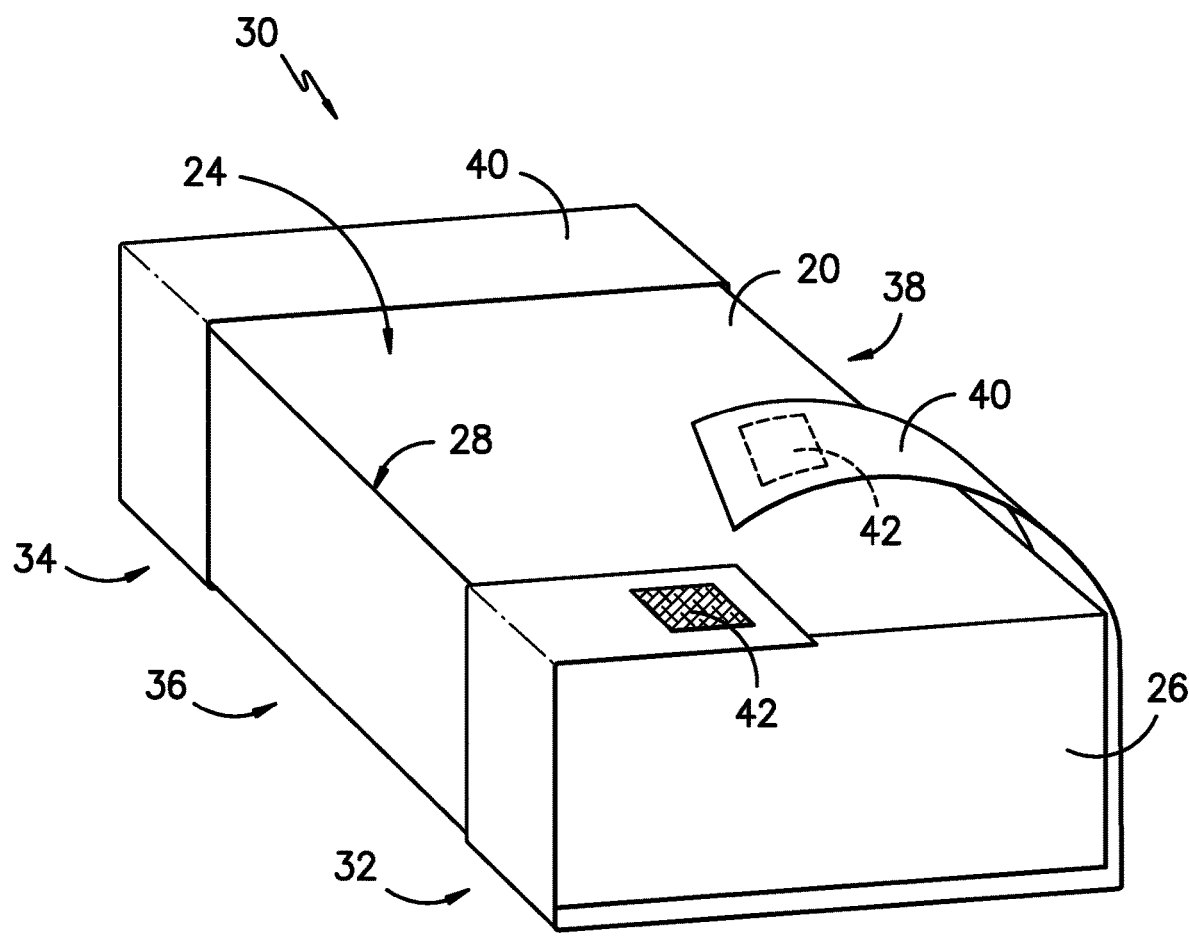
FIG. -2-
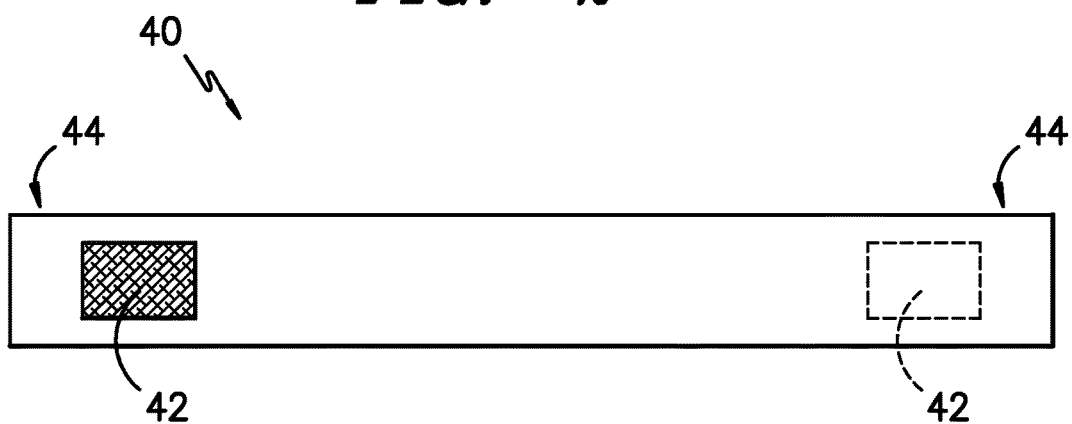
FIG. -3-

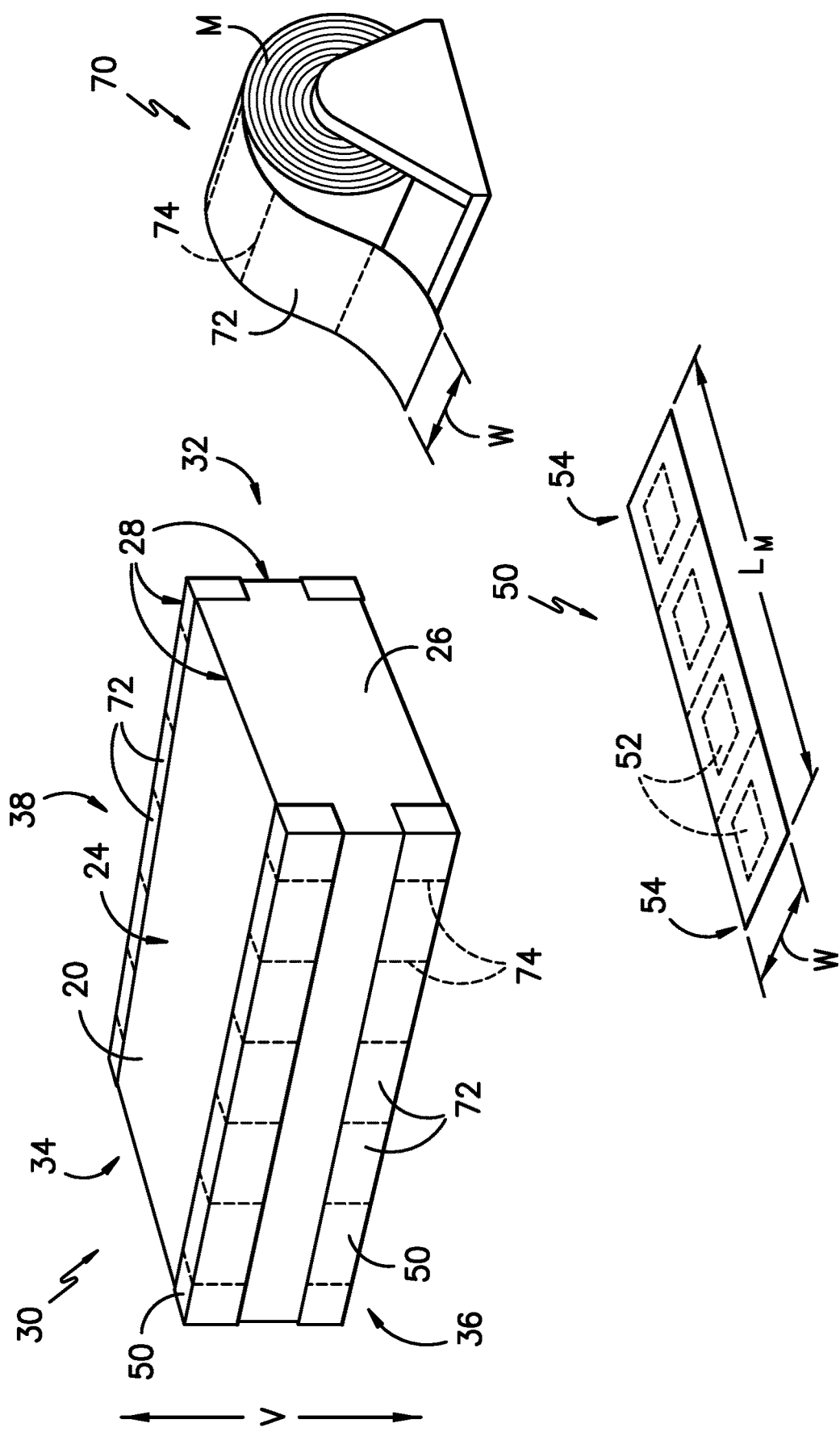
FIG. -4-

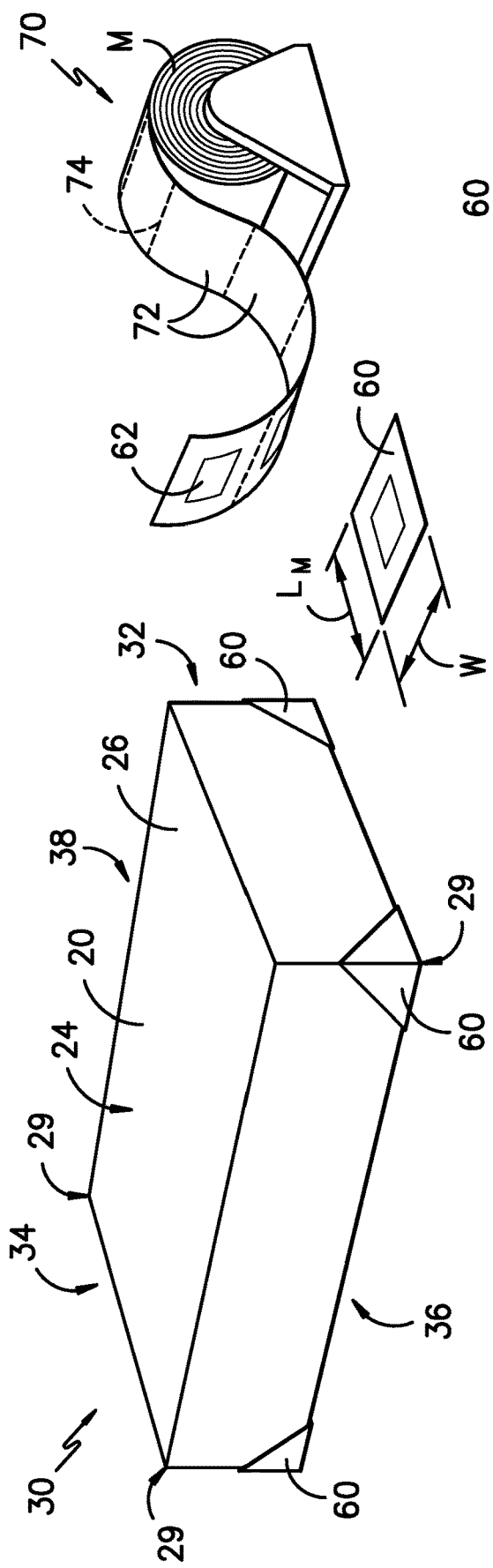
FIG. -5-
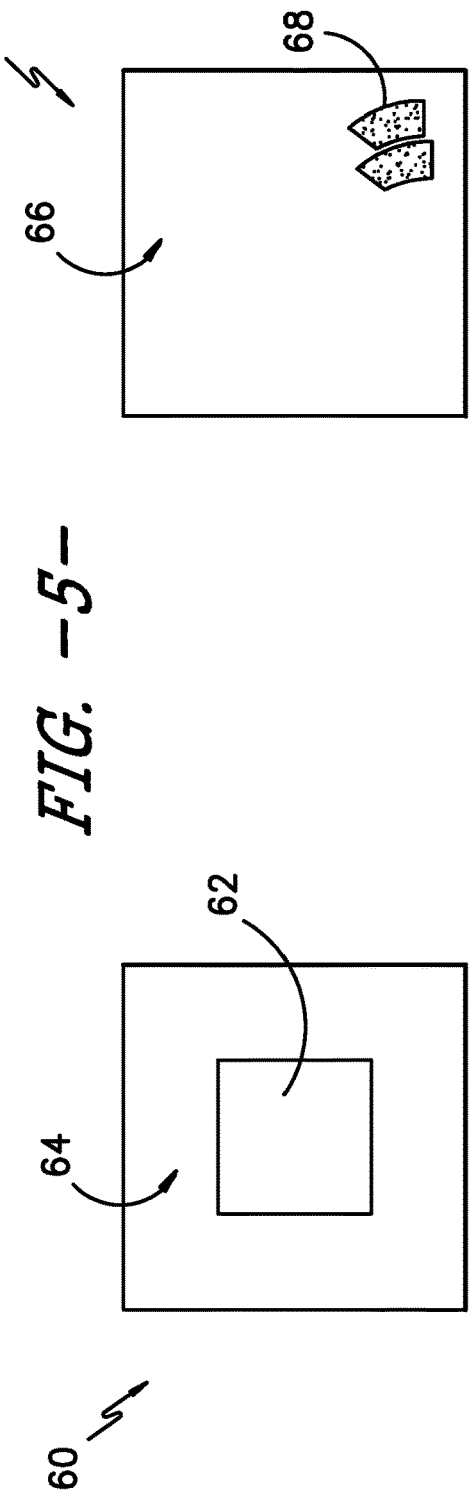
FIG. -7-
FIG. -6-

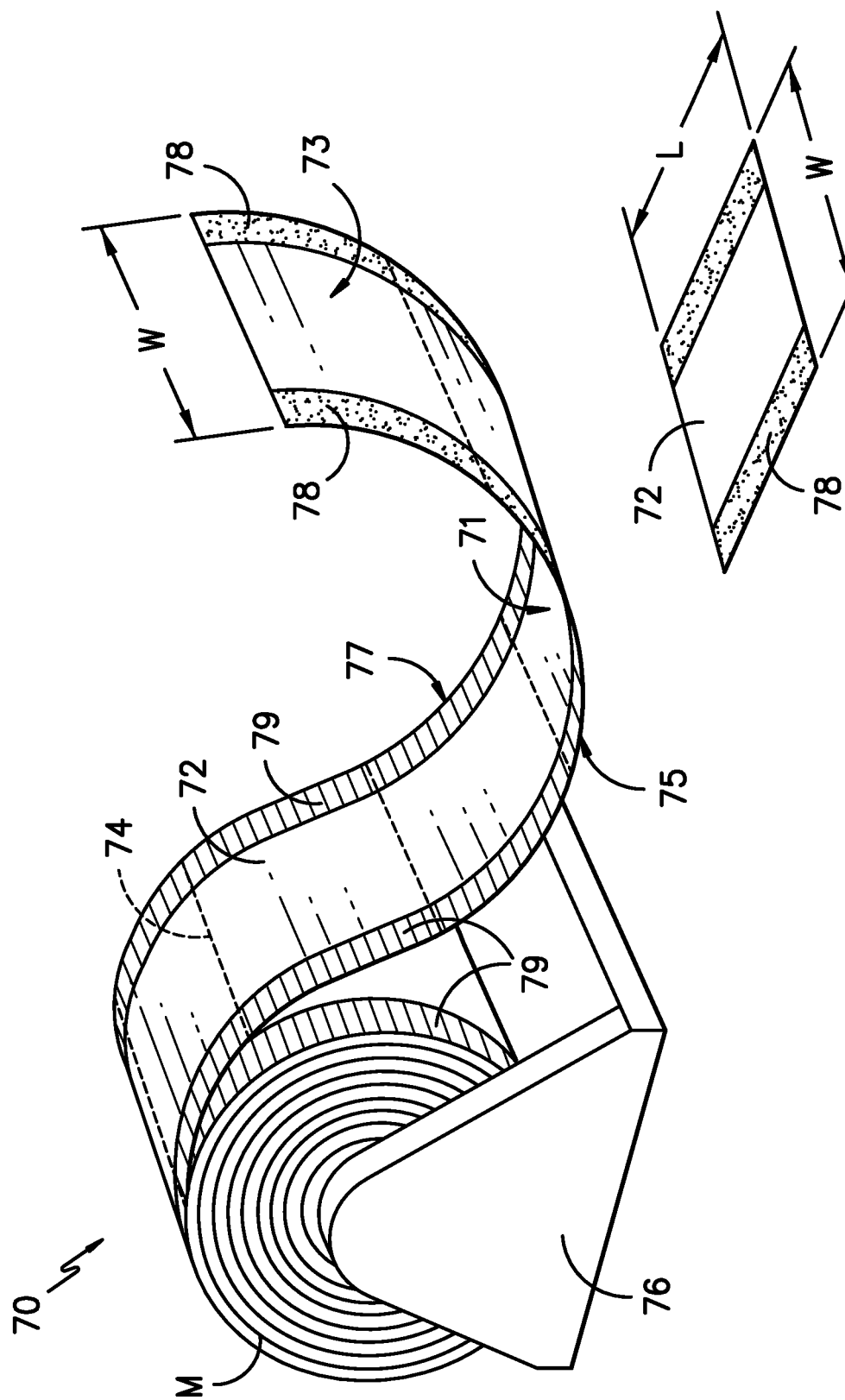
FIG. -8-

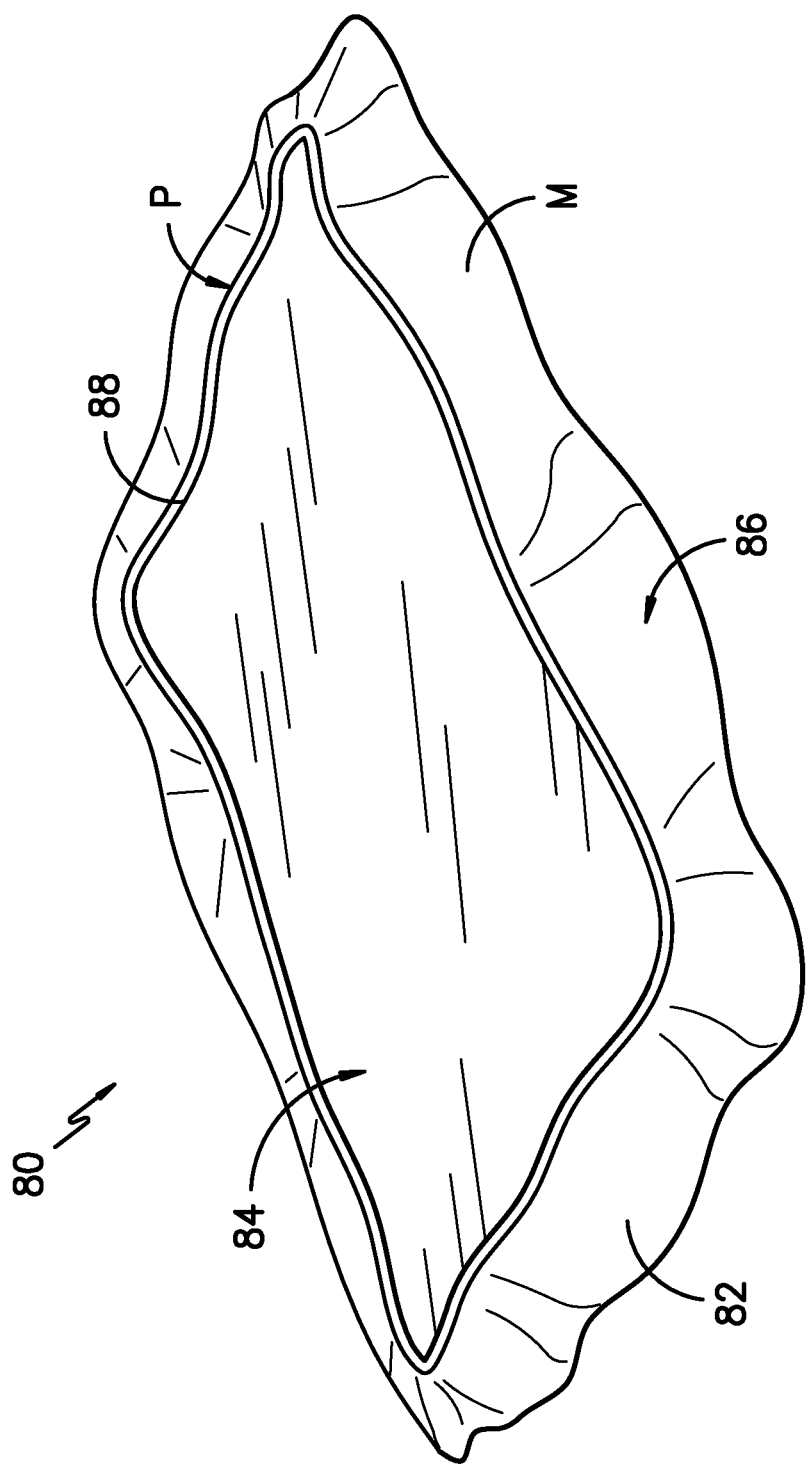
FIG. -9-

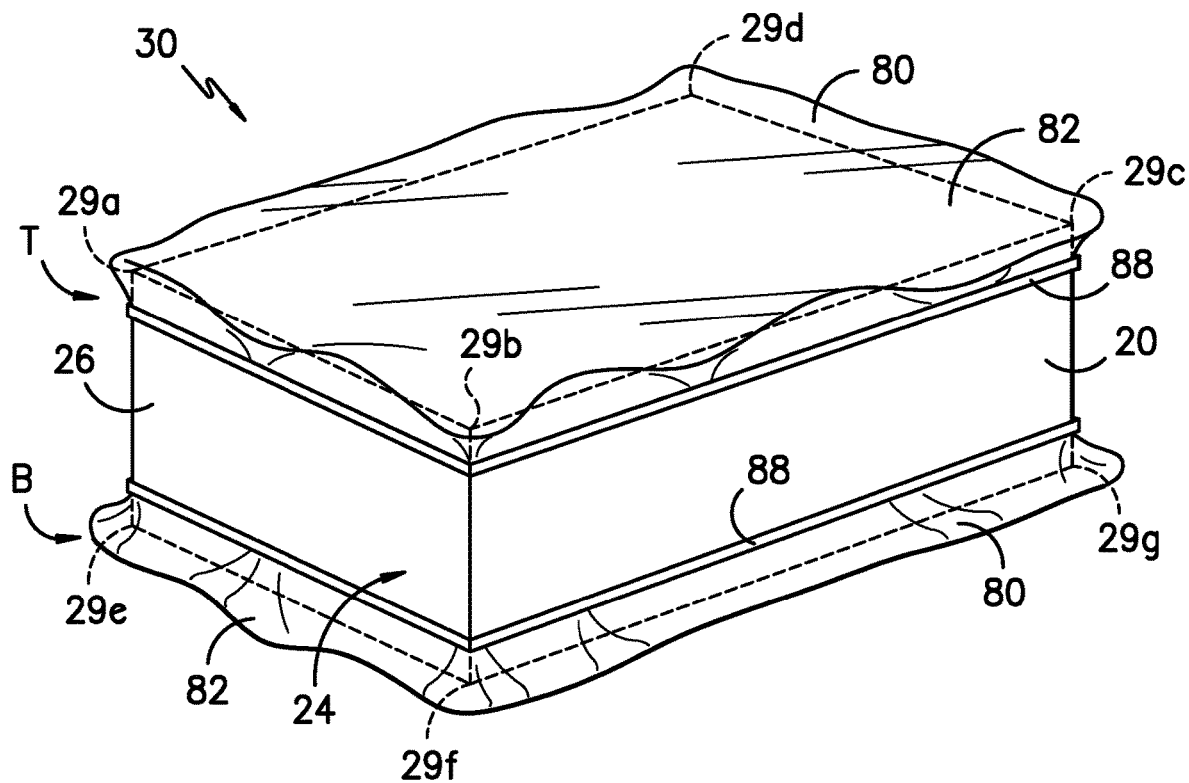
FIG. -10-
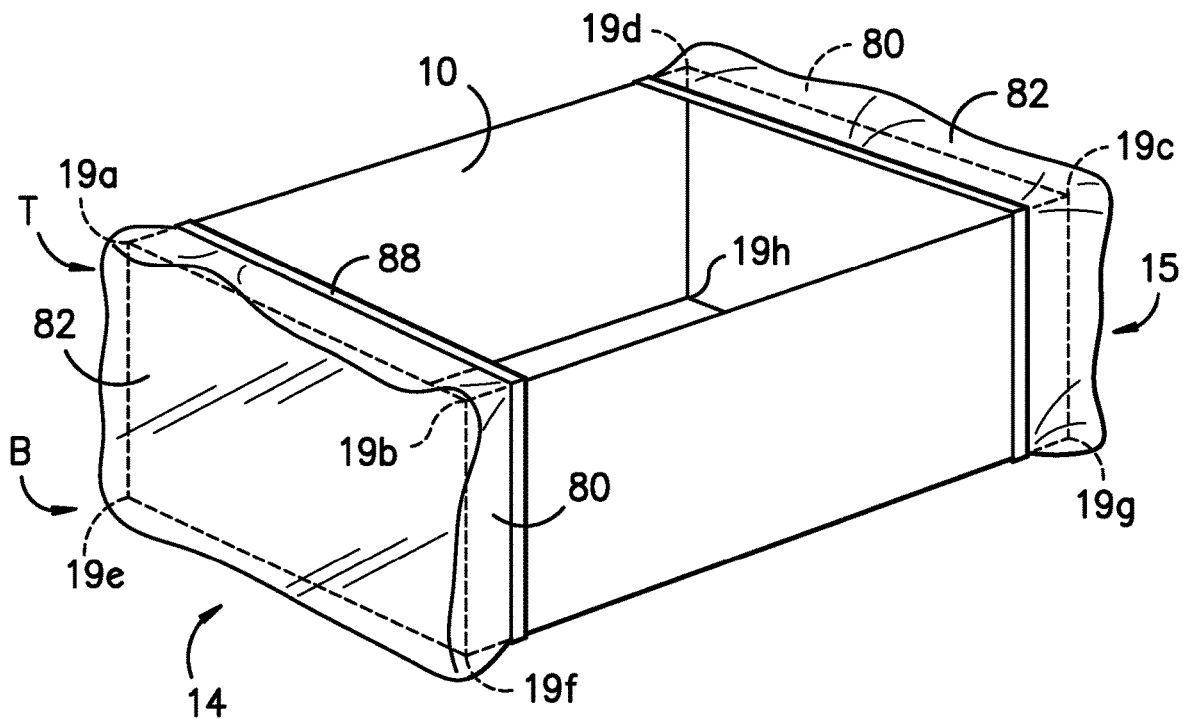
FIG. -11-

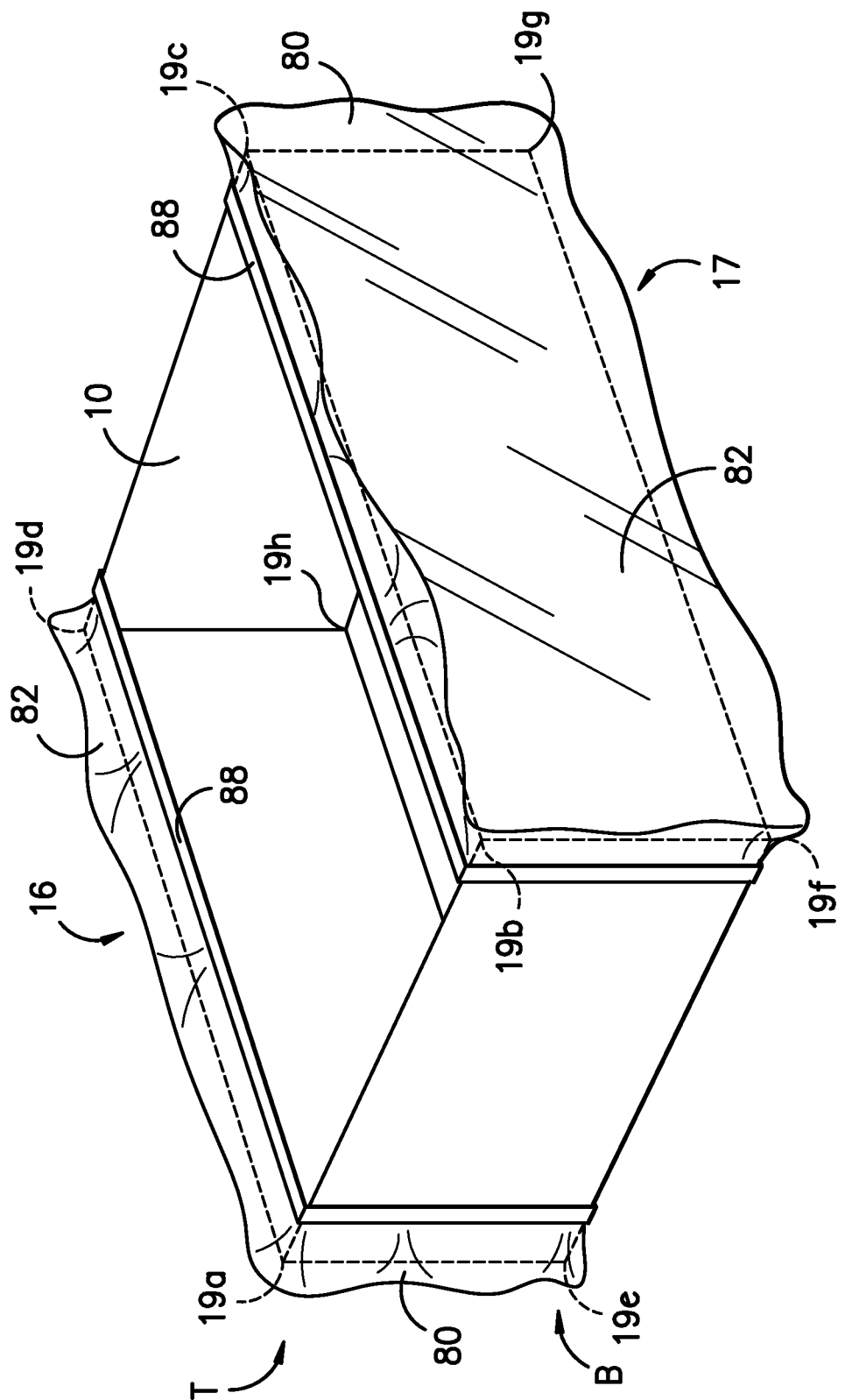
FIG. -12-

STERILIZATION TRAY PROTECTION MECHANISMS

CROSS-REFERENCE TO RELATED APPLICATIONS

This application is a national phase of and claims priority to PCT/US2015/044957, filed Aug. 13, 2015, the contents of which are incorporated herein by reference thereto.

FIELD OF THE INVENTION

The subject matter of the present disclosure relates generally to sterilization packaging and sterilization packaging systems.

BACKGROUND

Personnel in the Central Service Room (CSR) or the Sterile Processing Department (SPD) of hospitals are commonly charged with the responsibility of packaging surgical supplies to ensure that the sterility of the packaged contents is maintained from sterilization to the point of reuse. Several activities are involved in the task of sterile supply delivery to the operating room and other units.

Much of the surgical instruments and supplies used in the operating room are reusable. These supplies typically include such things as clamps, scalpel blade handles, retractors, forceps, scissors, surgeon's towels, basins, and the like. All of these supplies must be collected after each procedure, decontaminated, placed in a sterilization packaging system, and sterilized before they can be used again in another procedure. The sterilization packaging systems used must be of the size and shape to accommodate the items to be sterilized and must be compatible with and withstand the physical conditions of the sterilization process.

Common sterilization packaging systems include sealable pouches and sterilization wraps. Generally, sterilization pouches are used for small, lightweight objects. A sterilization pouch is made of flexible materials that are formed into a pouch having an open end, and the instrument to be sterilized is placed into the pouch through the open end. The open end is typically sealed closed with an adhesive strip or a peelable heat seal. Examples of such sterilization pouches can be found in U.S. Pat. No. 5,459,978 to Weiss et al. and in U.S. Pat. No. 3,991,881 to Augurt.

Alternatively, sterilization wrap generally is used for the sterilization of larger, heavier, and/or irregularly shaped objects. In particular, sterilization wrap is used to wrap sterilization trays containing several objects; often, the tray will contain all of the instruments needed for a single particular medical procedure and can weigh between 5 and 25 pounds. Generally, metal supplies are placed in stainless steel sterilization trays, while soft goods such as surgeon's towels, drapes, and gowns are wrapped directly. The sterilization wrap usually is a woven or nonwoven material, and when wrapped around the tray or package contents, the tray or package contents are fully enclosed within the folds of the wrap. Wrapping in a certain prescribed manner will permit the entry of sterilizing vapor/gas or other medium to sterilize the contents of the tray while denying the ingress of contaminants such as bacteria and other infectious causing materials or their vehicles after sterilization.

To promote and maintain the sterility of the packaged contents, the Association of Operating Room Nurses (AORN) has developed certain recommended practices for the wrapping and handling of in-hospital processed packages. As recommended by the AORN, It is common practice among many hospitals to "double wrap" in-hospital processed packages with two layers of barrier material. Doubling wrapping minimizes the probability of a breach due to a flaw in any one layer of material. Products have been developed that reduce the labor required in simultaneous wrapping by joining an outer and inner layer such that the layers can be manipulated as a unitary laminate wrapper. For example, one such product is KIMGUARD® ONE-STEP® produced by Kimberly-Clark Corporation, which is generally described, for example, in U.S. Pat. Nos. 5,635,134 and 5,688,476. Other such two-ply sterilization wraps can be found U.S. Pat. No. 6,406,764 to Bayer and U.S. Pat. No. 6,517,916 to Bayer et al.

Common means of sterilizing instruments include, among others, autoclaving with steam, exposure to ethylene oxide gas, and exposure to hydrogen peroxide plasma, as is done with the STERRAD® Sterilization System from Advanced Sterilization Products, Irvine, Calif. After the wrapped tray and its contents have been sterilized, the wrapped tray typically is stored until it is needed for a surgical procedure.

Once needed, the wrapped tray is transported to the point of use, typically an operating room. During storage and transfer to the operating room, the wrapped tray may be handled several different times. Each time the wrapped package is handled, there is a potential that the sterile nature of the package contents can be compromised. The two most common ways the wrapped package can be compromised are a tear or other breach of the wrapping material and/or wetness or foreign materials identified on the outer wrapper. When a sterile package is compromised, it must be re-processed, e.g., it must be taken out of circulation, unwrapped, rewrapped, and resterilized with a new sterilization wrapper or it must undergo immediate use sterilization before it can properly be reused. Re-processing packages wastes time and money and could negatively impact patients, e.g., by delaying the start of a surgery or requiring a patient to remain under anesthesia while a package is re-processed or a sterilized package is located.

The method of wrapping helps keep the sterilization package sealed. Selecting an adequately sized sterilization wrap having good drapeability and making crisp folds and tucks, according to the wrapping practice used, helps keep the sterilization wrap folded about the items to be sterilized. Additionally, the loose ends of the sterilization wrap that remain after making the final fold can be secured with an attachment mechanism such as, e.g., a piece of adhesive tape. Accordingly, the method of wrapping can help minimize breaches of the wrapping material and reduce the number of compromised packages.

However, the edges and corners of the wrapped package remain susceptible to tears, cuts, holes, or other breaches of the wrapping material. These tears, cuts, etc. may occur on the interior and/or the exterior of the sterilization wrap while in use on a wrapped package. Moreover, unprotected or inadequately protected corners and edges of the tray could be damaged, e.g., scratched, dented, or the like. Double wrapping the packages as previously described can reduce the possibility of such tears, etc., but double wrapping requires additional material and wrapping time, which can increase the cost of wrapping each package, e.g., by unnecessarily increasing the basis weight of material used in the sterilization wrap system. Further, previous attempts to protect the sterilization wrap have required the use of, e.g., molded plastic or polymer pieces that can increase the cost of the sterilization wrap system and can themselves tear or cut the sterilization wrap.

Consequently, there is a need for a sterilization wrap system that reduces the likelihood of re-processing from cuts, tears, and the like to the wrapping material. A sterilization wrap system that reduces tears, cuts, and other breaches of the wrapping material while minimizing the costs of and the material required for the sterilization wrap system also would be beneficial. Additionally, a sterilization wrap system that protects the sterilization tray from scratches, cuts, and the like would be advantageous.

SUMMARY

The present invention provides a sterilization wrap system with features for protecting a sterilization wrap and/or a sterilization tray of the sterilization wrap system. Such features include strap or belt protectors, edge protectors, corner protectors, and/or expandable protectors, which each may provide protection of one or more areas of the sterilization wrap and/or sterilization tray when positioned against an outer surface of the wrap and/or between an inner surface of the wrap and a container for holding implements to be sterilized. The present invention also provides a size-selectable protection system. The size-selectable protection system provides a material having a plurality of perforations such that a length of the material may be selected and detached from the rest of the material. The selected length of material may be used with a sterilization wrap system to protect a sterilization wrap and/or sterilization tray from cuts, tears, or the like. Additional aspects and advantages of the invention will be set forth in part in the following description, may be apparent from the description, or may be learned through practice of the invention.

In a first exemplary embodiment, a sterilization wrap system is provided. The sterilization wrap system includes a sterilization wrap having an inner surface and an outer surface; one or more corner protectors positioned adjacent one or more corners of a package wrapped with the sterilization wrap; and an attachment mechanism for attaching the corner protectors to the sterilization wrap or to a tray for holding implements to be sterilized. The sterilization wrap and the corner protectors are made from a substantially similar material.

In a second exemplary embodiment, a size-selectable protection system for a sterilization wrap is provided. The size-selectable protection system includes a material having an overall length, a width, a first surface, and a second surface; a plurality of perforations extending across the width of the material, the perforations spaced apart along the length of the material to define a plurality of sections of the material; an attachment mechanism provided on the first surface of the material; and a release mechanism provided on the second surface of the material such that the release mechanism is provided on the second surface opposite the attachment mechanism provided on the first surface. The release mechanism is configured such that the attachment mechanism does not attach to the release mechanism. A length of the material may be selected and detached from the overall length of the material, and the length of the material may be used with a sterilization wrap to protect the sterilization wrap.

In a third exemplary embodiment, a corner protector for a sterilization wrap system is provided. The corner protector includes a first surface; a second surface opposite the first surface; and an attachment mechanism. The corner protector is essentially flat.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 provides a perspective view of an exemplary sterilization container or tray and an exemplary sterilization wrap prior to wrapping the container or tray for sterilization.

FIG. 2 provides a perspective view of a sterilization wrap system according to an exemplary embodiment of the present subject matter.

FIG. 3 provides a top view of a strap or belt protector according to an exemplary embodiment of the present subject matter.

FIG. 4 provides a perspective view of a sterilization wrap system according to another exemplary embodiment of the present subject matter.

FIG. 5 provides a perspective view of a sterilization wrap system according to another exemplary embodiment of the present subject matter.

FIG. 6 provides a top view of one surface of a corner protector according to an exemplary embodiment of the present subject matter.

FIG. 7 provides a top view of another surface of the corner protector of FIG. 6.

FIG. 8 provides a perspective view of a size-selectable protection system according to an exemplary embodiment of the present subject matter.

FIG. 9 provides a perspective view of an expandable protector according to an exemplary embodiment of the present subject matter.

FIG. 10 provides a perspective view of a sterilization wrap system according to another exemplary embodiment of the present subject matter.

FIG. 11 provides a perspective view of a portion of a sterilization wrap system according to another exemplary embodiment of the present subject matter.

FIG. 12 provides a perspective view of a portion of a sterilization wrap system according to another exemplary embodiment of the present subject matter.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Described herein is a sterilization wrap system and components thereof suitable for use in a variety of procedures for wrapping, sterilizing, storing, and using sterilized items such as surgical supplies. While described in conjunction with its use in hospital and surgical room procedures, the present subject matter is intended for use wherever there is a need for sterilized materials. Consequently, the following description should not be considered a limitation as to the scope of use of the present subject matter.

FIG. 1 provides a perspective view of an exemplary sterilization container or tray 10 and an exemplary sterilization wrap 20 prior to wrapping tray 10 for sterilization. To wrap an item for sterilization, such as sterilization tray 10 holding one or more implements 12 to be sterilized, the item is placed on top of sterilization wrap 20 in contact with an inner surface 22 of sterilization wrap 20 such that the four corners of sterilization wrap 20 can be folded over the item one at a time to fully wrap the item and form a wrapped package 26 (FIG. 2). During and after this wrapping, sterilization tray 10 would only come into contact with inner surface 22 of sterilization wrap 20. After wrapping, an outer surface 24 (FIG. 2) of sterilization wrap 20 forms the resulting exterior surfaces of wrapped item or package 26. Thus, inner surface 22 of wrap 20 faces tray 10, and outer surface 24 of wrap 20 opposes inner surface 22 and faces away from tray 10.

Sterilization wrap 20 must be of a size large enough to fully wrap the items to be sterilized. Generally, sterilization wraps 20 come in several sizes to wrap various size items and trays. Typical sizes include 18, 24, 30, 36, 40, 45, 48 and 54 inch square sheets; as well as 54 inch by 72 inch rectangular sheets; other sizes also may be used. Usually, each fold of the sterilization wrap 20 folds over most of the item to be sterilized, and each subsequent fold overlaps the previous fold, leaving the item to be sterilized completely encompassed within the folds of sterilization wrap 20.

Once wrapped, the finished wrapped package can then be transferred to sterilizing equipment and exposed to sterilization conditions. Such sterilization conditions can include, e.g., steam, ethylene oxide, or hydrogen peroxide plasma sterilization conditions. Sterilization conditions are the conditions present during a particular sterilization methodology utilized that substantially or completely destroys bacteria and other infectious organisms in an industrial or medical product.

Typically, a sealing mechanism, such as one or more of an adhesive, tape, mechanical fastener, or the like, is applied to sterilization wrap 20 to hold the folds of wrap 20 in place. The sealing mechanism can be present on the sterilization wrap 20 in various locations and configurations. The exact location and configuration can be designed to best address the method of wrapping. For example, the sealing mechanism could be placed in one or more discrete areas or locations on sterilization wrap 20, such as, e.g., in one or more corners of wrap 20. Further, the sealing mechanism may be appropriate size, shape, or means for facilitating sealing of the wrapped item or package within sterilization wrap 20. For example, the sealing mechanism may be an adhesive and/or a mechanical fastening element, such as, e.g., interlocking geometric shaped materials, such as hooks, loops, bulbs, mushrooms, arrowheads, balls on stems, male and female mating components, clips, buckles, snaps, buttons, or the like. In some embodiments, one or more sealing mechanisms may be used, such as a combination of an adhesive and a mechanical fastening element or a combination of different mechanical fastening elements. As one example, the presence of both an adhesive strip and mechanical fastening means gives added options in terms of how sterilization wrap 20 can be held securely closed until exposed to sterilization conditions.

Also, the sealing mechanism may be formulated so that when exposed to sterilization conditions, the sealing mechanism is activated to form or strengthen bonds that keep the wrapped package in a completely wrapped configuration, also known as a "closed" configuration. This closed configuration denies ingress of contaminants due to both the barrier properties of the sterilization wrap material and the tortuous path created by the folds of sterilization wrap 20.

Sterilization wrap 20 can be made from a number of materials. The sheets of sterilization wrap systems are generally characterized as falling into two main classes, reusables and disposables. Reusables are materials that, as the name suggests, can be reused, typically by washing or some other form of cleaning. Disposables, on the other hand, are usually one-use items that are discarded or recycled after their initial use. Generally, cloth, linen, or other woven materials fall into the reusable category while disposables normally include nonwoven materials made from either or both natural and synthetic fibers such as paper, fibrous polymeric nonwovens, and films, which are capable of passing sterilants and retarding transmission of bacteria and other contaminants.

Nonwoven sterilization wraps have become particularly well-liked due to their barrier properties, economics and consistent quality. The nonwoven materials can be made from a variety of processes including, but not limited to, air laying processes, wet laid processes, hydroentangling processes, spunbonding, meltblowing, staple fiber carding and bonding, and solution spinning. The fibers themselves can be made from a variety of both natural and synthetic materials including, but not limited to, cellulose, rayon, nylon, polyesters, polyolefins and many other materials. The fibers may be relatively short, staple length fibers, typically less than three inches, or longer and substantially more continuous fibers such as are produced by spunbonding and meltblowing processes. Whatever materials are chosen, the resultant wrap must be compatible with the particular sterilization technique being used and must also provide both strength and barrier properties to maintain the sterile nature of the wrapped contents until use.

It has been found that polyolefin-based fibers and their resultant nonwovens are particularly well-suited for the production of sterilization wrap. Polypropylene spunbonded nonwovens such as are produced by Halyard Health, Inc. of Alpharetta, Ga., can be used to impart strength characteristics to sterilization wrap 20. In some embodiments, sterilization wrap 20 may be made from laminates such as a laminate of spunbonded and meltblown or spunbonded, meltblown, spunbonded to impart both strength and barrier properties to sterilization wrap 20.

A spunbonded-meltblown-spunbonded material is made from three separate layers that are laminated to one another. The method of making these layers is known and described in U.S. Pat. No. 4,041,203 to Brock, et al., which is incorporated herein in its entirety by reference. The material of Brock, et al. is a three layer laminate of spunbonded-meltblown-spunbonded layers that is also commonly referred to by the acronym "SMS." The two outer layers of SMS are a spunbonded material made from extruded polyolefin fibers, or filaments, laid down in a random pattern and then bonded to one another. The inner layer is a meltblown layer also made from extruded polyolefin fibers generally of a smaller diameter than the fibers in the spunbonded layers. As a result, the meltblown layer provides increased barrier properties due to its fine fiber structure, which permits the sterilizing agent to pass through the fabric while preventing passage of bacteria and other contaminants. Conversely, the two outer spunbonded layers provide a greater portion of the strength factor in the overall laminate. The laminate may be prepared using an intermittent bond pattern that is preferably employed with the pattern being substantially regularly repeating over the surface of the laminate. The pattern is selected such that the bonds may occupy about 5% to about 50% of the surface area of the laminate. Desirably, the bonds may occupy about 10% to about 30% of the surface area of the laminate.

Referring now to FIG. 2, a perspective view is provided of a sterilization wrap system 30 according to an exemplary embodiment of the present subject matter. In the embodiment shown in FIG. 2, sterilization wrap system 30 includes sterilization wrap 20 and two sterilization strap or belt protectors 40 encircling ends 32, 34 of wrapped package 26. In other embodiments, protectors 40 may encircle one or both sides 36, 38 of wrapped package 26, or protectors 40 may be positioned to wrap around other portions of package 26. In still other embodiments, strap or belt protectors 40 may be provided on inner surface 22 of sterilization wrap 20 or on the items to be sterilized. As an example, a protector 40 may be provided directly on sterilization tray 10 (FIG. 1), e.g., on each end 14, 15 and/or each side 16, 17 of sterilization tray 10, such that protector 40 lies between sterilization tray 10 and inner surface 22 of sterilization wrap 20 when tray 10 is wrapped with sterilization wrap 20.

Strap or belt protectors 40 may be provided to protect edges and/or corners of sterilization wrap 20 from cuts, tears, and the like that could cause contaminants to enter wrapped package 26. More particularly, protector 40 may be positioned against outer surface 24 of sterilization wrap 20 and/or between inner surface 22 of wrap 20 and sterilization tray 10 at a location of wrap 20 that is susceptible to sustaining cuts, tears, or other breaches of wrap 20. In this position, as an example, protector 40 could sustain cuts and/or tears rather than sterilization wrap 20 sustaining cuts and/or tears. As a further example, protector 40 could provide an extra layer of material such that, even if sterilization wrap 20 is cut or torn, wrapped package 26 is not breached. Similarly, strap or belt protectors 40 may be provided to protect the edges and/or corners of sterilization tray 10 from scratches, cuts, dents, and the like. Thus, strap or belt protector 40 helps prevent cuts or tears to sterilization wrap 20 and/or tray 10; protectors 40 also may help prevent the ingress of contaminants if wrap 20 is cut or torn. One of ordinary skill should readily understand that any configuration and positioning of strap or belt protectors 40 could be used to protect sterilization wrap 20 and/or tray 10 as needed or desired.

Two protectors 40 are provided in FIG. 2 only by way of example; any other number of strap or belt protectors 40 may be used. In some embodiments, protectors 40 are made of the same material or a substantially similar as sterilization wrap 20. For example, strap protector or belt protector 40 may be made from a SMS, breathable film, or other nonwoven material similar to or the same as the material from which wrap 20 is made such that protector 40 and wrap 20 may both be discarded after use. In other embodiments, protector 40 and wrap 20 may be made from different materials; the material from which each is constructed may be selected such that protector 40 and wrap 20 are both disposable or reusable as desired, or one of protector 40 and wrap 20 may be disposable and the other may be reusable. As one example, sterilization wrap 20 may be made from a SMS nonwoven material and protector 40 may be made from a breathable film. Suitable films for the construction of protector 40 may include highly porous or perforated films or film laminates. Strap or belt protectors 40 also may be made from an elastic or stretchy material such that each protector 40 may stretch to fit about and then rest snugly against wrapped package 26 or sterilization tray 10. Protectors 40 also may be made from any other appropriate material such that protectors 40 are either disposable or reusable as desired.

As shown in FIG. 3, each strap or belt protector 40 may be generally flat when not wrapped about or encircling sterilization tray 10 and/or wrapped package 26. That is, protector 40 generally is a piece of material having two parallel planar surfaces that are opposed to each other. The piece of material also may be generally rectangular in shape such that each protector 40 is substantially rectangular in shape. In an exemplary embodiment, each strap or belt protector 40 may be approximately 30 inches in length and approximately 4 inches in width. In alternative embodiments, protector 40 may have other lengths and widths; appropriate lengths and widths of protector 40 may be provided for a variety of sizes of sterilization tray 10 and/or wrapped package 26. In still other embodiments, each protector 40 may be a continuous band of material that may be slipped onto an end 32, 34 or side 36, 38 of wrapped package 26 to encircle package 26 or onto an end 14, 15 or side 16, 17 of tray 10 to encircle tray 10. In such embodiments, the material forming protector 40 may have an appropriate width, and protector 40 may have an appropriate diameter for encircling wrapped package 26 and/or tray 10 to provide protection to the edges and/or corners of sterilization wrap 20 and/or tray 10.

Further, strap or belt protector 40 may include one or more attachment mechanisms 42 for attaching protector 40 to sterilization wrap 20 and/or sterilization tray 10. Attachment mechanisms 42 may be configured such that protector 40 is repositionable with respect to sterilization wrap 20 and/or sterilization tray 10. In the exemplary embodiment of strap or belt protector 40 illustrated in FIG. 3, an attachment mechanism 42 is included at each end 44 of protector 40. However, any appropriate number, position, or configuration of attachment mechanisms 42 may be used.

Attachment mechanisms 42 may be adhesives, such as double-sided tape or the like, or other non-mechanical fasteners. For example, as previously described, strap or belt protector 40 may be a continuous band that is slipped onto sterilization tray 10 or wrapped package 26, such that attachment mechanism 42 is an elastic or expandable material incorporated into protector 40, or attachment mechanism 42 is an elastic or expandable property of the material from which protector 40 is made. That is, strap or belt protector 40 attaches or is secured to tray 10 or package 26 due to its elastic or expandable properties or due to the incorporation of an elastic or expandable component into protector 40. In other embodiments, any appropriate mechanical fastening means may be used, e.g., interlocking geometric shaped materials, such as hooks, loops, bulbs, mushrooms, arrowheads, balls on stems, male and female mating components, clips, buckles, snaps, buttons, or the like. In some embodiments, attachment mechanism 42 may include a fastening component and a mating fastening component, e.g., hook-and-loop fastening components. In still other embodiments, attachment mechanism 42 may attach directly to strap or belt protector 40, inner or outer surfaces 22, 24 of sterilization wrap 20, and/or sterilization trap 10. That is, attachment mechanism 42 may comprise a fastening component without a corresponding mating fastening component.

In particular embodiments, attachment mechanism 42 may comprise hook elements formed in strap or belt protector 40, i.e., the hook elements are integral with protector 40. As an example, the hook elements may be heat formed in the material of protector 40. In such embodiments, the hook elements may be formed at one or more locations on protector 40, e.g., at both ends 44 of protector 40 as shown in FIG. 3. Further, the hooks may be formed such that the hooks are oriented in a direction that enhances their ability to secure, attach, or fasten strap or belt protector 40 about sterilization tray 10 and/or wrapped package 26. For example, if wrapped package 26 is jostled in a certain direction, the hooks are oriented to more securely engage or fasten to sterilization wrap 20 and/or a mating fastening component, such as an element comprising a plurality of loops, positioned on sterilization tray 10. Of course, one skilled in the art will recognize that, if a hook-and-loop type mechanism is chosen for attachment mechanism 42, the shape, density, and polymer composition of the hooks and loops may be selected to obtain the desired level of fastening between the hooks and the loops.

Referring now to FIG. 4, a perspective view is provided of a sterilization wrap system 30 according to another exemplary embodiment of the present subject matter. In the embodiment shown in FIG. 4, sterilization wrap system 30 includes sterilization wrap 20 and a plurality of edge protectors 50 positioned along edges 28 of wrapped package 26, i.e., each edge protector 50 is attached to outer surface 24 of sterilization wrap 20 adjacent an edge 28 of package 26. In other embodiments, protectors 50 may be positioned along other edges 28 of wrapped package 26, and in some embodiments, edge protectors 50 may be provided on every edge 28 of wrapped package 26. In still other embodiments, edge protectors 50 may be provided on inner surface 22 of sterilization wrap 20 or on the items to be sterilized. As an example, an edge protector 50 may be provided directly on one or more edges 18 of sterilization tray 10 (FIG. 1) such that edge protectors 50 lie between sterilization tray 10 and inner surface 22 of sterilization wrap 20 when tray 10 is wrapped with sterilization wrap 20. As another example, one or more edge protectors 50 may be attached to inner surface 22 of sterilization wrap 20 prior to wrapping package 26 such that each edge protector 50 is attached to sterilization wrap 20 at a location that is adjacent to an edge 28 of package 26 when the package is wrapped with sterilization wrap 20.

Edge protectors 50 may be provided to protect edges and/or corners of sterilization wrap 20 from cuts, tears, and the like that could cause contaminants to enter wrapped package 26. More particularly, one or more edge protectors 50 may be positioned against outer surface 24 of sterilization wrap 20 and/or between inner surface 22 of wrap 20 and sterilization tray 10 at a location of wrap 20 that is susceptible to sustaining cuts, tears, or other breaches of wrap 20. Accordingly, as an example, protector 50, rather than sterilization wrap 20, could sustain cuts and/or tears. As a further example, protector 50 could provide an extra layer of material such that, even if sterilization wrap 20 is cut or torn, wrapped package 26 is not breached. Similarly, strap or belt protectors 40 may be provided to protect the edges and/or corners of sterilization tray 10 from scratches, cuts, dents, and the like. Thus, edge protector 50 helps prevent cuts or tears to sterilization wrap 20 and/or tray 20; edge protector 50 also may help prevent the ingress of contaminants if wrap 20 is cut or torn. It should be readily understood that any configuration and positioning of edge protectors 50 could be used to protect sterilization wrap 20 and/or tray 10 as needed or desired.

The configuration of edge protectors 50 shown in FIG. 4 is provided only by way of example; any other number and position of edge protectors 50 may be used, e.g., edge protectors 50 may also be positioned along vertical edges 28 (i.e., edges 28 extending along the vertical direction V) of wrapped package 26. In some embodiments, protectors 50 are made of the same or a substantially similar material as sterilization wrap 20. As an example, each edge protector 50 may be made from a SMS, breathable film, or other non-woven material similar to or the same as the material from which wrap 20 is made such that protectors 50 and wrap 20 may both be discarded after use. In other embodiments, protector 50 and wrap 20 may be made from different materials; the material from which each is constructed may be selected such that protector 50 and wrap 20 are both disposable or reusable as desired, or one of protector 50 and wrap 20 may be disposable and the other may be reusable. As one example, sterilization wrap 20 may be made from a SMS nonwoven material and protector 50 may be made from a breathable film. Suitable films for the construction of edge protectors 50 may include highly porous or perforated films or film laminates. Edge protectors 50 also may be made from an elastic or stretchy material such that each protector 50 may stretch along an edge 28 of wrapped package 26 or sterilization tray 10. Moreover, edge protectors 50 may be made from a generally flexible material such that each edge protector 50 can conform to the shape of an edge of wrapped package 26 and/or sterilization tray 10. Protectors 50 also may be made from any other appropriate material such that protectors 50 are either disposable or reusable as desired.

As further shown in FIG. 4, each edge protector 50 may be essentially flat when not positioned along an edge of sterilization tray 10 and/or wrapped package 26. That is, protector 50 generally is a piece of material having two parallel planar surfaces that are opposed to each other. The piece of material also may be generally rectangular in shape such that each protector 50 is substantially rectangular in shape. In an exemplary embodiment, each edge protector 50 may be approximately 18 to 20 inches in length and approximately 4 inches in width. Alternatively, protector 50 may have other lengths and widths; appropriate lengths and widths of protector 50 may be provided for a variety of sizes of sterilization tray 10 and/or wrapped package 26. Moreover, in some embodiments, edge protector 50 may be configured similar to strap or belt protector 40 such that edge protector 50 is configured to wrap around or encircle wrapped package 26 and/or sterilization tray 10. For example, edge protector 50 may be configured to wrap widthwise and/or lengthwise around wrapped package 26 and/or sterilization tray 10, i.e., around a side or an end of package 26 and/or tray 10 like the exemplary strap or belt protector 40 shown in FIG. 2. In embodiments wherein edge protector 50 is configured similar to strap or belt protector 40, edge protector 50 may be positioned to maximize the amount of material of protector 50 adjacent to edges 28 of wrapped package 26 to protect sterilization wrap 20 particularly along edges 28. However, any portion of edge protector 50 not adjacent an edge 28 also may assist in protecting sterilization wrap 20 from cuts, tears, or the like. In other embodiments, protector 50 may be positioned to protect sterilization tray 10 particularly along edges 18, but portions of protector 50 not adjacent an edge 18 also may protect tray 10 from cuts, scratches, and the like.

In still other embodiments, each edge protector 50 may be selected from a size-selectable protection system 70. Protection system 70 may comprise an overall length of material M having a width W. Protection system 70 may further comprise a plurality of sections 72 defined by perforations 74 extending across width W of material M. In some embodiments, perforations 74 may be equally spaced apart along the overall length of material M such that each section 72 has the same length L (FIG. 8), but in other embodiments, perforations 74 may be unequally spaced along the overall length of material M such that sections 72 are of varying lengths L. Using size-selectable protection system 70, an appropriate length $L_M$ of material M may be selected for each edge protector 50, where the length $L_M$ or material M may comprise one or more sections 72 of material M. As an example, the selected length $L_M$ of material M may be greater than width W of material M. Size-selectable protection system 70 is discussed more fully below.

Each edge protector 50 may include one or more attachment mechanisms 52 for attaching edge protector 50 to sterilization wrap 20 and/or sterilization tray 10. Attachment mechanism 52 may be configured such that edge protector 50 is repositionable with respect to sterilization wrap 20 and/or sterilization tray 10. Further, in some embodiments, an attachment mechanism 52 may be included at each end 54 of edge protector 50 or along one or more edges of each edge protector 50. However, any appropriate number, position, or configuration of attachment mechanisms 52 may be used.

Attachment mechanism 52 may be an adhesive, such as double-sided tape or the like, or another non-mechanical fastener. In other embodiments, any appropriate mechanical fastening means may be used, e.g., interlocking geometric shaped materials, such as hooks, loops, bulbs, mushrooms, arrowheads, balls on stems, male and female mating components, clips, buckles, snaps, buttons, or the like. In some embodiments, attachment mechanism 52 may include a fastening component and a mating fastening component, e.g., hook-and-loop fastening components. In still other embodiments, attachment mechanism 52 may attach directly to or engage directly with inner or outer surfaces 22, 24 of sterilization wrap 20 or sterilization trap 10. That is, attachment mechanism 52 may comprise a fastening component without a corresponding mating fastening component. For example, attachment mechanism 52 may be a plurality of hook elements positioned on edge protector 50, where the hooks are configured to engage the material from which sterilization wrap 20 is made. The present subject matter also encompasses means for attaching edge protector 50 to sterilization wrap 20 and/or sterilization tray 10 in which attachment mechanism 52 may be one or more mechanical fastening systems and/or adhesives used separately or together.

In particular embodiments, attachment mechanism 52 may comprise a plurality of hook elements formed in edge protector 50, as previously described with respect to strap or belt protector 40. For example, hook elements may be integrally formed in edge protector 50, e.g., by heat forming or other appropriate means, at one or more locations on edge protector 50. Further, the hooks may be formed such that the hooks are oriented in a direction that enhances their ability to secure, attach, or fasten edge protector 50 to sterilization wrap 20 and/or a mating fastening component, such as an element comprising a plurality of loops, positioned on sterilization tray 10. It will be readily understood that other forms of hook-and-loop type fasteners may be selected for attachment mechanism 52, where the shape, density, and polymer composition of the hooks and loops may be selected to obtain the desired level of fastening between the hooks and the loops.

Referring now to FIG. 5, a perspective view is provided of a sterilization wrap system 30 according to another exemplary embodiment of the present subject matter. In the embodiment shown in FIG. 5, sterilization wrap system 30 includes sterilization wrap 20 and a plurality of corner protectors 60 positioned at corners 29 of wrapped package 26, i.e., each illustrated corner protector 60 is attached to outer surface 24 of sterilization wrap 20 adjacent corners 29 at a bottom portion B of package 26. In other embodiments, protectors 60 may be positioned at other corners 29 of wrapped package 26, and in some embodiments, corner protectors 60 may be provided on every corner 29 of wrapped package 26. In still other embodiments, corner protectors 60 may be provided on inner surface 22 of sterilization wrap 20 or on the items to be sterilized. As an example, a corner protector 60 may be provided directly on one or more corners 19 of sterilization tray 10 (FIG. 1) such that corner protectors 60 lie between sterilization tray 10 and inner surface 22 of sterilization wrap 20 when tray 10 is wrapped with sterilization wrap 20. As another example, one or more corner protectors 60 may be attached to inner surface 22 of sterilization wrap 20 prior to wrapping package 26 such that each corner protector 60 is attached to sterilization wrap 20 at a location that is adjacent to a corner 29 of package 26 when the package is wrapped with sterilization wrap 20.

Like strap or belt protector 40 and edge protector 50, corner protectors 60 may be provided to protect corners of sterilization wrap 20 from cuts, tears, and the like that could cause contaminants to enter wrapped package 26. More specifically, one or more corner protectors 60 may be positioned against outer surface 24 of sterilization wrap 20 and/or between inner surface 22 of wrap 20 and sterilization tray 10 at a location of wrap 20 that is susceptible to sustaining cuts, tears, or other breaches of wrap 20. Being so positioned, corner protector 60 could, for example, sustain cuts and/or tears rather than sterilization wrap 20 sustaining cuts and/or tears. As another example, protector 60 could provide an extra layer of material such that, even if sterilization wrap 20 is cut or torn, wrapped package 26 is not breached. Similarly, corner protectors 60 may be provided to protect the corners of sterilization tray 10 from scratches, cuts, dents, and the like. Thus, corner protector 60 helps prevent cuts or tears to sterilization wrap 20 and/or tray 10. Corner protector 60 also may help prevent the ingress of contaminants if wrap 20 is cut or torn. Of course, one of ordinary skill will recognize that any configuration and positioning of corner protectors 60 could be used to protect sterilization wrap 20 and/or tray 10 as needed or desired.

The configuration of corner protectors 60 shown in FIG. 5 is provided only by way of example; any other number and position of corner protectors 60 may be used. In some embodiments, protectors 60 are made of the same or a substantially similar material as sterilization wrap 20. For example, each corner protector 60 may be made from a SMS, breathable film, or other nonwoven material similar to or the same as the material from which wrap 20 is made such that protectors 60 and wrap 20 may both be discarded after use. In other embodiments, protector 60 and wrap 20 may be made from different materials; the material from which each is constructed may be selected such that protector 60 and wrap 20 are both disposable or reusable as desired, or one of protector 60 and wrap 20 may be disposable and the other may be reusable. As one example, sterilization wrap 20 may be made from a SMS nonwoven material and corner protector 60 may be made from a breathable film. Suitable films for the construction of corner protectors 60 may include highly porous or perforated films or film laminates. Corner protectors 60 also may be made from an elastic or stretchy material such that corner protectors 60 may stretch to fit corners 29 of wrapped package 26 or corners 19 of sterilization tray 10. Moreover, corner protectors 60 may be made from a generally flexible material such that each corner protector 60 can conform to the shape of a corner of wrapped package 26 and/or sterilization tray 10. Protectors 60 also may be made from any other appropriate material such that protectors 60 are either disposable or reusable as desired.

As shown in FIG. 6, each corner protector 60 may be essentially flat when not positioned at a corner of sterilization tray 10 and/or wrapped package 26. That is, protector 60 generally is a piece of material having two parallel planar surfaces that are opposed to each other. The piece of material also may be generally square in shape such that each protector 60 is substantially square in shape, i.e., the length may be generally equal to the width of each protector 60. For example, each corner protector 60 may be an approximately 4 inch by 4 inch square. In alternative embodiments, corner protectors 60 may have other lengths and widths, i.e., the length and width may be different; appropriate lengths and widths of protector 60 may be provided for a variety of sizes of sterilization tray 10 and/or wrapped package 26. Further, corner protectors 60 may have other appropriate shapes or configurations, e.g., each corner protector 60 may be generally circular in shape or have a polygonal shape other than rectangular.

In still other embodiments, corner protectors 60 may be selected from size-selectable protection system 70. As previously described, protection system 70 may comprise an overall length of material M having a width W, with a plurality of sections 72 defined by perforations 74 extending across width W of material M. In some embodiments, perforations 74 may be equally spaced apart along the overall length of material M such that each section 72 has the same length L (FIG. 8), but in other embodiments, perforations 74 may be unequally spaced along the overall length of material M such that sections 72 are of varying lengths L. Each section 72 may form a corner protector 60, i.e., one section 72 may be selected to protect one corner of the package wrapped with sterilization wrap 20. However, in other embodiments, each corner protector 60 may comprise one or more sections 72 of material M, i.e., using size-selectable protection system 70, an appropriate length $L_M$ of material M may be selected for each corner protector 60.

Each corner protector 60 may include one or more attachment mechanisms 62 for attaching corner protector 60 to sterilization wrap 20 and/or sterilization tray 10. Attachment mechanism 62 may be configured such that corner protector 60 is repositionable with respect to sterilization wrap 20 and/or sterilization tray 10. As illustrated in the exemplary embodiment of FIG. 6, an attachment mechanism 62 may be included generally in the middle of corner protector 60. However, any appropriate number, position, or configuration of attachment mechanisms 62 may be used, e.g., an attachment mechanism 62 could be included at each corner of corner protector 60 or along one or more edges of each corner protector 60.

Attachment mechanism 62 may be an adhesive, such as double-sided tape or the like, or other non-mechanical fasteners. In other embodiments, any appropriate mechanical fastening means may be used, e.g., interlocking geometric shaped materials, such as hooks, loops, bulbs, mushrooms, arrowheads, balls on stems, male and female mating components, clips, buckles, snaps, buttons, or the like. In some embodiments, attachment mechanism 62 may include a fastening component and a mating fastening component, e.g., hook-and-loop fastening components. In still other embodiments, attachment mechanism 62 may attach directly to or engage directly with inner or outer surfaces 22, 24 of sterilization wrap 20 or sterilization trap 10. That is, attachment mechanism 62 may comprise a fastening component without a corresponding mating fastening component. For example, attachment mechanism 62 may be a plurality of hook elements positioned on corner protector 60, where the hooks are configured to engage the material from which sterilization wrap 20 is made. Of course, the present subject matter also encompasses means for attaching corner protector 60 to sterilization wrap 20 and/or sterilization tray 10 in which attachment mechanism 62 may be one or more mechanical fastening systems and/or adhesives used separately or together.

In particular embodiments, attachment mechanism 62 may comprise a plurality of hook elements formed in corner protector 60, as previously described with respect to strap or belt protector 40 and edge protector 50. For example, hook elements may be integrally formed in corner protector 60, e.g., by heat forming or other appropriate means, at one or more locations on corner protector 60. Further, the hooks may be formed such that the hooks are oriented in a direction that enhances their ability to secure, attach, or fasten corner protector 60 to sterilization wrap 20 and/or a mating fastening component, such as an element comprising a plurality of loops, positioned on sterilization tray 10. Of course, one skilled in the art will recognize that, if a hook-and-loop type mechanism is chosen for attachment mechanism 62, the shape, density, and polymer composition of the hooks and loops may be selected to obtain the desired level of fastening between the hooks and the loops.

Continuing with the exemplary embodiment of sterilization wrap system 30 illustrated in FIGS. 5, 6, and 7, corner protector 60 includes a first surface 64 and a second surface 66 opposite first surface 64. An indicator ink 68 may be printed on one or both of first surface 64 and second surface 66 of corner protector 60. Indicator ink 68 may be configured to indicate whether the package wrapped with sterilization wrap 20, such as wrapped package 26, has been sterilized. For example, indicator ink 68 may be formulated to change in color or phase upon sterilization, which would allow a user of sterilization wrap system 30 to visually determine from observing corner protector 60 whether or not corner protector 60 having indicator ink 68, and thus sterilization wrap system 30, has been or needs to be exposed to sterilization conditions. Indicator ink 68 may be printed on or otherwise applied to corner protector 60 in any desired or appropriate pattern or shape, including but not limited to geometric shapes, logos, words, phrases, and the like. An exemplary shape or configuration of indicator ink 68 is illustrated in FIG. 7; the shape could be larger or repeated across second surface 66 such that indicator ink 68 covers a large or substantial portion of second surface 66 of corner protector 60. Indicator ink 68 also may be provided on one or more surfaces of strap or belt protector 40, edge protector 50, and expandable protector 80 described below. Other embodiments and/or configurations of indicator ink 68 may be used as well.

Referring now to FIG. 8, a perspective view is provided of size-selectable protection system 70 according to an exemplary embodiment of the present subject matter. As previously described, protection system 70 may comprise an overall length of material M having a width W. Material M may be a nonwoven material, such as a SMS, highly porous or perforated film, film laminate, or other nonwoven material, but other types of materials may be used as well. The overall or total length of material M may be gathered in a roll form such that a length $L_M$ of material M may be selected from the overall length by unrolling material M. More particularly, the roll of material M may be supported on a frame 76 that facilitates the unrolling or dispensing of material M. The selected length $L_M$ of material M may be detached from the overall length of material M along a perforation 74 that extends across width W of material M. Accordingly, the overall or total length of material M decreases as lengths $L_M$ of the material are selected and detached from the overall length of material M.

As described, a plurality of perforations 74 are formed or provided in material M, and perforations 74 define a plurality of sections 72 along the overall length of material M. Each section 72 may have the same length L, or alternatively, sections 72 may have varying lengths L. In some embodiments, length L of each section 72 may be approximately equal to width W of material M such that each section 72 of material M is approximately square-shaped. In other embodiments, length L of each section 72 may be different from width W of material M. The selected length $L_M$ of material M may comprise one or more sections 72 of size-selectable protection system 70. Further, as previously described, length $L_M$ of material M may be selected for an edge protector 50 and/or a corner protector 60, as desired. In appropriate embodiments, a length $L_M$ of material M also may be selected to form a strap or belt protector 40.

Material M may have a first surface 71 and an opposing second surface 73, with a first edge 75 extending along the overall length of material M and a second edge 77 extending along the overall length of material M. As shown in FIG. 8, an attachment mechanism 78, such as an adhesive or other appropriate attachment mechanism, may be applied to second surface 73 along first and second edges 75, 77 of material M. Correspondingly, a release mechanism 79, such as a non-stick coating or the like, may be applied to first surface 71 along first and second edges 75, 77 of material M.

Attachment mechanism 78 allows length $L_M$ of material M to attach to sterilization wrap 20 and/or sterilization tray 10 to protect sterilization wrap 20 from cuts, tears, or the like that can introduce contaminants to a sterilized package wrapped with sterilization wrap 20 and/or to protect sterilization tray 10 from damage such as scratches, cuts, and the like. Thus, attachment mechanism 78 may be any appropriate attachment mechanism as previously described with respect to attachment mechanisms 42, 52, and 62. Release mechanism 79 facilitates gathering material M in roll form by preventing attachment mechanism 78 from attaching to material M. That is, release mechanism 79 is applied or provided on material M such that attachment mechanism 78 contacts release mechanism 79 rather than material M when material M is rolled up. Release mechanism 79 is configured such that attachment mechanism 78 does not attach to release mechanism 79 to provide easy, smooth unrolling of material M to select lengths $L_M$ of material M. The material, composition, and/or construction of release mechanism 79 may be selected for a particular attachment mechanism 78. As an example, attachment mechanism 78 may be an adhesive, and release mechanism 79 may be a non-stick coating to which the adhesive does not stick or with which the adhesive does not engage such that the adhesive does not and cannot attach to the non-stick coating.

It should be readily understood that the configuration of attachment mechanism 78 and release mechanism 79 shown in FIG. 8 is by way of example only. In other embodiments, attachment mechanism 78 may be applied or provided at another position on material M, and release mechanism 79 is applied or provided at an appropriate position or location to prevent attachment mechanism 78 from attaching to or engaging material M. For example, attachment mechanism 78 may be applied on first surface 71 and/or second surface 73 of material M. Further, attachment mechanism 78 may be applied along at least one of first and second edges 75, 77, in the middle of each section 72, at the corners of each section 72, and/or at any other appropriate location on material M.

As appropriate, attachment mechanism 42, 52, 62, 78 may be selected to release in a particular fashion after it has been sterilized. For example, attachment mechanism 42, 52, 62, 78 may be an adhesive formulated to degrade under sterilization conditions such that strap or belt protector 40, edge protector 50, corner protector 60, and/or selected length $L_M$ of material M is easily removed after sterilization of wrapped package 26. As another example, attachment mechanism 42, 52, 62, 78 may be an adhesive formulated to release upon exposure to a chemical reaction or energy, such as UV wavelength radiation. Alternatively, attachment mechanism 42, 52, 62, 78 may be formulated or selected to peel away from the substrate to which it attaches, e.g., sterilization wrap 20 and/or sterilization tray 10, upon application of certain level of force or application of force in a particular direction. Any combination of such functionalities and/or additional functionalities may be incorporated in the formulation of attachment mechanism 42, 52, 62, 78.

FIG. 9 provides a perspective view of an exemplary expandable protector 80 that may be used in a sterilization wrap system 30 of the present subject matter. As shown, a covering portion 82 comprising a piece of material M having a first surface 84 and a second surface 86 may be provided with one or more expandable portions 88. Material M may be a nonwoven material, such as a SMS, highly porous or perforated film, film laminate, or other nonwoven material, but other types of materials may be used as well. In some embodiments, material M may be expandable or stretchy. Material M may be the same or substantially similar to the material used to make the sterilization wrap 20 of sterilization wrap system 30, but in alternative embodiments, expandable protector 80 and wrap 20 may be made from different materials. Material M may be selected such that expandable protector 80 is disposable, or material M may be selected such that expandable protector 80 is reusable.

Expandable portions 88 may be localized with respect to covering portion 82 such that covering portion 82 is expandable in particular areas. In some embodiments, expandable portion 88 may form a generally continuous loop about covering portion 82, such that expandable portion 88 extends along or defines a perimeter P of covering portion 82. In other embodiments, several expandable portions 88 may be provided along perimeter P of covering portion 82 such that a length of material M extends between each expandable portion 88. As an example, four expandable portions 88 may be provided along perimeter P such that expandable portions 88 generally define or are positioned at corners of covering portion 82. Expandable portion 88 may be made from any appropriate material, such as an elastic or the like.

Referring now to FIGS. 10, 11, and 12, various exemplary embodiments of sterilization wrap system 30 are illustrated. In the exemplary embodiment shown in FIG. 10, sterilization wrap system 30 includes sterilization wrap 20 and two expandable protectors 80 to protect a top portion T and a bottom portion B of sterilization wrap 20 and/or sterilization tray 10. As illustrated, protectors 80 are positioned to surround corners 29 of top portion T and bottom portion B. That is, one expandable protector 80 is positioned against outer surface 24 of sterilization wrap 20 such that covering portion 82 of expandable protector 80 surrounds the top four corners 29a, 29b, 29c, and 29d of package 26. A second expandable protector 80 is positioned against outer surface 24 of sterilization wrap 20 such that covering portion 82 of expandable protector 80 surrounds the top four corners 29e, 29f, 29g, and 29h (not shown) of package 26. Expandable portion or portions 88 of each expandable protector 80 may expand to position protector 80 against wrap 20 and contract to hold protector 80 in place against wrap 20. In alternative embodiments, one or more expandable protectors 80 may be positioned on sterilization tray 10 to surround corners 19 of tray 10. Expandable portion or portions 88 of each expandable protector 80 may hold the protector in place against tray 10. Then, sterilization wrap 20 may be wrapped about tray 10 such that expandable protector or protectors 80 are positioned between wrap 20 and tray 10.

In the exemplary embodiment of FIG. 11, to protect sterilization wrap 20 along the ends of a package wrapped with wrap 20 and/or to protect sterilization tray 10 along its ends, two expandable protectors 80 are positioned to surround corners 19 of first end 14 and second end 15 of tray 10 for holding implements 12 (FIG. 1). As shown, one expandable protector 80 is positioned against tray 10 such that covering portion 82 of expandable protector 80 surrounds two top corners 19a and 19b and two bottom corners 19e and 19f of tray 10. A second expandable protector 80 is positioned against sterilization tray 10 such that covering portion 82 of expandable protector 80 surrounds two top corners 19c and 19d and two bottom corners 19g and 19h of tray 10. Expandable portion or portions 88 of each expandable protector 80 may expand to position protector 80 against tray 10 and contract to hold protector 80 in place against tray 10. In other embodiments, one or more expandable protectors 80 may be positioned against outer surface 24 of sterilization wrap 20 when wrap 20 is wrapped about sterilization tray 10 to form wrapped package 26 such that each expandable protector 80 extends along an end of package 26 and surrounds two top corners 29 and two bottom corners 29 of package 26. Expandable portion or portions 88 of each expandable protector 80 may hold protector 80 in place against wrap 20.

As illustrated in the exemplary embodiment of FIG. 12, expandable protectors 80 may also be positioned to protect sterilization wrap 20 along the sides of a package wrapped with wrap 20 and/or to protect the sides of sterilization tray 10. As shown, two expandable protectors 80 are positioned to surround corners 19 of first side 16 and second side 17 of tray 10 for holding implements 12 (FIG. 1) to be sterilized. One expandable protector 80 is positioned against tray 10 such that covering portion 82 of expandable protector 80 surrounds two top corners 19a and 19d and two bottom corners 19e and 19h of tray 10. A second expandable protector 80 is positioned against sterilization tray 10 such that covering portion 82 of expandable protector 80 surrounds two top corners 19b and 19c and two bottom corners 19f and 19g of tray 10. Expandable portion or portions 88 of each expandable protector 80 may expand to position protector 80 against tray 10 and contract to hold protector 80 in place against tray 10. In other embodiments, one or more expandable protectors 80 may be positioned against outer surface 24 of sterilization wrap 20 when wrap 20 is wrapped about sterilization tray 10 to form wrapped package 26 such that each expandable protector 80 extends along a side of package 26 and surrounds two top corners 29 and two bottom corners 29 of package 26. Expandable portion or portions 88 of each expandable protector 80 may hold protector 80 in place against wrap 20.

Similar to strap or belt protector 40, edge protector 50, and corner protector 60, expandable protector 80 may be provided to protect edges and/or corners of sterilization wrap 20 from cuts, tears, and the like that could cause contaminants to enter wrapped package 26. More particularly, one or more expandable protectors 80 may be positioned against outer surface 24 of sterilization wrap 20 or between inner surface 22 of wrap 20 and sterilization tray 10 at a location of wrap 20 that is susceptible to sustaining cuts, tears, or other breaches of wrap 20. Being so positioned, expandable protector 80 could, for example, sustain cuts and/or tears instead of sterilization wrap 20 sustaining cuts and/or tears. As another example, protector 80 could provide an extra layer of material such that, even if sterilization wrap 20 is cut or torn, wrapped package 26 is not breached. Similarly, one or more expandable protectors 80 may be provided to protect the edges and/or corners of sterilization tray 10 from scratches, cuts, dents, and the like. Thus, expandable protector 80 helps prevent cuts or tears to sterilization wrap 20 and/or tray 10 and also may help prevent the ingress of contaminants if wrap 20 is cut or torn. It should be readily understood that any configuration and positioning of expandable protectors 80 could be used to protect sterilization wrap 20 and/or tray 10 as needed or desired.

Although described separately, it should be understood that any protection mechanism described herein could be used separately or in combination with any other protection mechanism to assist in protecting sterilization wrap 20 and/or tray 10 from cuts, tears, or the like that could lead to contamination of a sterilized package. As an example, corner protectors 60 could be provided on each corner of sterilization tray 10 and, additionally, edge protectors 50 could be provided on outer surface 24 of sterilization wrap 20 wrapped about tray 10, i.e., on the edges of wrapped package 26. Other combinations of protectors 40, 50, 60, 80 may be used as well, and protectors 40, 50, 60, 80 also could be used in combination with other means for protecting sterilization wrap 20 and/or tray 10.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A sterilization wrap system comprising:
  a sterilization wrap having an inner surface and an outer surface; and
  a corner protector positioned adjacent a corner of a package wrapped with the sterilization wrap, the corner protector including an attachment mechanism for attaching the corner protector directly to the sterilization wrap,
  wherein the sterilization wrap and the corner protector are made from a same material.

2. The sterilization wrap system of claim 1, wherein the corner protector is essentially flat.

3. The sterilization wrap system of claim 1, wherein the corner protector is flexible to conform to the shape of a corner of the package.

4. The sterilization wrap system of claim 1, wherein the corner protector is attached to the inner surface of the sterilization wrap prior to wrapping the package, and wherein the corner protector is attached to the sterilization wrap at a location that will be adjacent a corner of the package.

5. The sterilization wrap system of claim 1, wherein the corner protector is attached to the outer surface of the sterilization wrap, and wherein the corner protector is attached adjacent a corner of the package.

6. The sterilization wrap system of claim 1, wherein the attachment mechanism is a plurality of hooks positioned on the corner protector, the plurality of hooks configured to engage the material from which the sterilization wrap and the corner protectors are made.

7. The sterilization wrap of claim 6, wherein the plurality of hooks are formed in the material from which the corner protectors is made.

\* \* \* \* \*